United States Patent
Garbini

(10) Patent No.: US 9,700,283 B2
(45) Date of Patent: Jul. 11, 2017

(54) VOLUME ULTRASOUND CATHETER ARRAY SUPPORT

(71) Applicant: Siemens Medical Solutions USA, Inc., Malvern, CA (US)

(72) Inventor: Lex J. Garbini, El Granada, CA (US)

(73) Assignee: SIEMENS MEDICAL SOLUTIONS USA, INC., Malvern, PA (US)

(*) Notice: Subject to any disclaimer, the term of this patent is extended or adjusted under 35 U.S.C. 154(b) by 117 days.

(21) Appl. No.: 14/166,697

(22) Filed: Jan. 28, 2014

(65) Prior Publication Data
US 2015/0209007 A1    Jul. 30, 2015

(51) Int. Cl.
*A61B 8/00* (2006.01)
*A61B 6/12* (2006.01)
*A61B 8/12* (2006.01)

(52) U.S. Cl.
CPC .............. *A61B 8/445* (2013.01); *A61B 6/12* (2013.01); *A61B 8/12* (2013.01); *Y10T 29/49005* (2015.01)

(58) Field of Classification Search
CPC ....................................................... A61B 8/00
USPC ........................................................ 600/459
See application file for complete search history.

(56) References Cited

U.S. PATENT DOCUMENTS

| 5,456,259 | A | * | 10/1995 | Barlow .................... A61B 8/12 600/459 |
| 5,779,639 | A | | 7/1998 | Yeung |
| 6,149,599 | A | | 11/2000 | Schlesinger et al. |
| 6,210,356 | B1 | | 4/2001 | Anderson et al. |
| 6,589,182 | B1 | | 7/2003 | Loftman et al. |
| 7,232,433 | B1 | * | 6/2007 | Schlesinger et al. ......... 604/527 |
| 2002/0022833 | A1 | * | 2/2002 | Maguire et al. ................ 606/27 |
| 2008/0125661 | A1 | * | 5/2008 | Garbini et al. ............... 600/459 |
| 2008/0294052 | A1 | * | 11/2008 | Wilser et al. ................. 600/459 |
| 2013/0199019 | A1 | | 8/2013 | Garbini et al. |

OTHER PUBLICATIONS

Martin et al (An ultrasonic catheter for intravascular measurement of blood flow: Technical details, 1980).*

* cited by examiner

*Primary Examiner* — Joel F Brutus

(57) ABSTRACT

A medical ultrasound imaging catheter is stiffened for introduction into the patient. An insert is mated with the array. The insert may stiffen the catheter at the array, avoiding damage due to buckling. The insert is keyed to the array in order to fix the orientation of the array, such as using a support for twisting the array as the key.

20 Claims, 4 Drawing Sheets

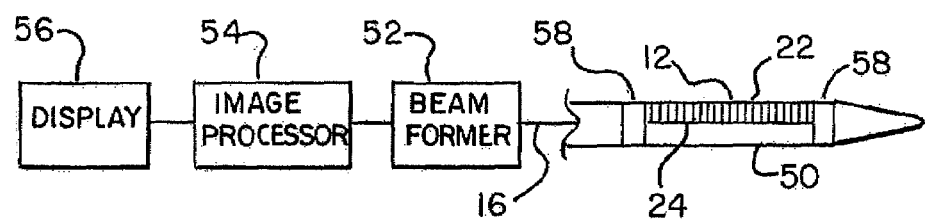
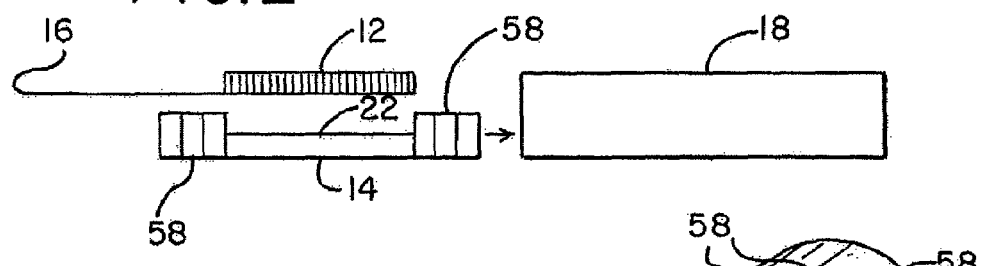
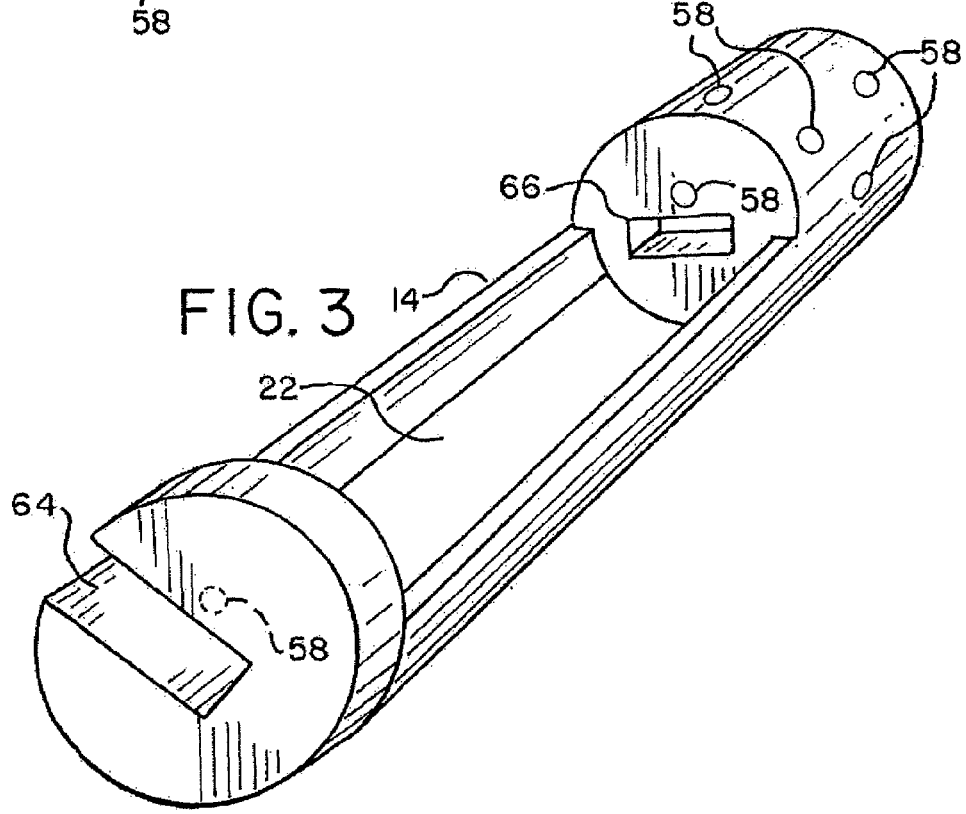

VOLUME ULTRASOUND CATHETER ARRAY SUPPORT

BACKGROUND

The present embodiments relate to medical ultrasound imaging catheters. A patient is scanned using an acoustic array of a catheter in the patient, providing real-time images from within the patient. The ultrasound imaging may assist with diagnosis or treatment. One such imaging catheter is a volume intra-cardiac echography (ICE) imaging catheter, the AcuNav V from Siemens. The array uses a helical twist of the face of the array to scan along different planes using different apertures.

To determine a position of the array in the patient, x-ray opaque markers in the catheter are detected with x-ray imaging (e.g., fluoroscopy). However, the relationship of the array to the markers must be known to relate the scan position of the array relative to the position of the catheter. To create the catheter, an acoustic array and markers are positioned in the catheter. Inexact positioning of the array in the catheter relative to the markers may cause misalignment problems.

The catheter is positioned in the patient through a guide or introducer. However, the catheter, and acoustic array in particular, may be damaged by insertion into a guide. For example, arrays with lengths of 7 mm or 14 mm may buckle, possibly damaging the array. Buckling of the array may adversely affect the safety and efficacy of the catheter. Longer arrays may allow for a scan of a larger volume, but may be more susceptible to buckling. Euler's formula for slender columns, where one end is fixed and the other end is free, is given as:

$$P = \frac{\pi^2 IE}{4L^2}$$

where P=total ultimate load, I=least moment of inertia, E=elastic modulus, and L=column length. This formula may be used to estimate the relative resistance to buckling as a function of array length. Assuming a solid cylinder, $$I = \frac{\pi d^4}{64}$$

where d=column diameter. Combining these equations yields:

$$P = \frac{\pi^3 d^4 E}{256 L^2} = \frac{kd^4}{L^2}$$

After normalizing to a given length (e.g., 7 mm), a 28 mm long array may have approximately 15% of the buckling resistance as compared to the array of the given length, even with a change in diameter from 10 Fr to 12.5 Fr. Longer arrays are more likely to suffer costly damage due to buckling when inserted into the patient.

BRIEF SUMMARY

By way of introduction, the preferred embodiments described below include methods, systems, and improvements for manufacturing a medical ultrasound imaging catheter, and resulting catheters. An insert is mated with the array using structure of the transducer array. For example, an extension from an end of a twisted array keys with a way in the insert. The insert may stiffen the catheter at the array, avoiding damage due to buckling. The insert is keyed to the array in order to fix the orientation of the array, such as using a support for twisting the array as the key.

In a first aspect, a method is provided for manufacturing a medical ultrasound imaging catheter. An insert is positioned adjacent to a transducer array with a keyed mating structure of the transducer array such that the transducer array is oriented relative to the insert. The transducer array is connected with the insert. A housing of the medical ultrasound imaging catheter is formed with the transducer array as oriented with the insert.

In a second aspect, a system is provided for manufacturing a medical ultrasound imaging catheter. A transducer array has a first shaped surface. A can has a second shaped surface keyed to the first shaped surface such that the transducer array mates with the can in a first orientation. A catheter housing connects with the can.

In a third aspect, a medical ultrasound imaging catheter includes a helical twisted array of acoustic elements mounted in a support with an orientation defined by at least two mating surfaces of the helical twisted array and the support. The mating surfaces include an extension and a matching depression. A housing connects with the support.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for use of a medical ultrasound imaging catheter;

FIG. 2 illustrates parts of a medical ultrasound imaging catheter according to one embodiment;

FIG. 3 is a perspective view of one embodiment of a can;

DETAILED DESCRIPTION OF THE DRAWINGS AND PRESENTLY PREFERRED EMBODIMENTS

Figure 4:
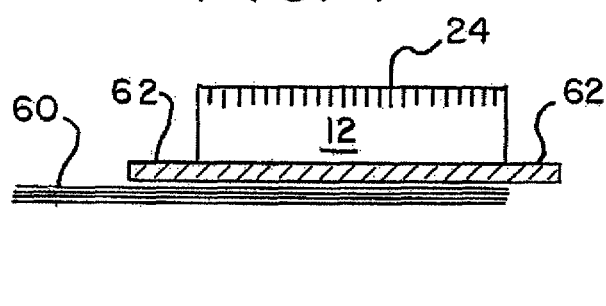
FIG. 4 is a side view of one embodiment of a keyed transducer array.

Greater dimensional stability is provided by incorporating a supporting member behind the array, such as behind a volume intra-cardiac echography (ICE) array. The supporting structure is a can, which increases the reliability of the catheter tip to withstand insertion of the catheter into the body through an introducer without bucking or bending the acoustic array. The support may increase the efficacy of catheters built with longer arrays. The maintenance of the straightness of the array may improve acoustic performance. The can provides an accurate framework for positioning x-ray opaque markers for image fusion, such as with ultrasound and CT. Keying of the can to the array results in reliable positioning of the array relative to the markers, resulting in more accurate image fusion or location determination of the scan region relative to the patient. The can may provide a framework for reducing electro-magnetic interference (EMI) or radio frequency interference (RFI) effects.

FIG. 1 shows a system for medical ultrasound imaging with a medical ultrasound imaging catheter having markers 58. The ultrasound imaging system is used for diagnosis and/or treatment in combination with another imaging modality, such as an x-ray, fluoroscopy, magnetic resonance, computed tomography, or optical system. Both imaging modalities scan a patient for generating images to assist a physician. The data from the different modalities is aligned by locating the markers 58 with a known spatial relationship to the ultrasound scan in the images of the other modality. In other embodiments, the system uses a catheter without the markers 58 and/or without another imaging modality.

The ultrasound imaging system includes the array 12 of elements 24 for medical ultrasound, a beamformer 52, an image processor 54, and a display 56. Additional, different, or fewer components may be provided. For example, the system includes the array 12 in a catheter 50 without the beamformer 52, image processor 54, and/or display 56. These imaging electronics may be in a separate ultrasound imaging system. The transducer and catheter 50 releasably connect with the imaging system.

The array 12 is used in a transducer probe, such as a medical ultrasound transducer. The transducer is used within a patient, such as a catheter 50, a transesophageal, vaginal, intercavity, intraoperative, or other probe. Alternatively, the transducer probe is used outside of a patient, such as a handheld transducer probe. The array 12 is connected with or positioned in the transducer probe. An acoustic window or lens covers the array 12 to allow acoustic scanning from an emitting face of the array 12 from within the probe. In the catheter embodiments, the window is the housing of the catheter 50.

The array 12 has a plurality of elements 24, backing block, electrodes, and a matching layer. Additional, different, or fewer components may be provided. For example, two or more matching layers are used. The backing block material absorbs acoustic energy to limit or prevent reflections received from the back of the array 12. The matching layers provide a more gradual transition between acoustic impedance, minimizing reflection from the boundary between the transducer and the patient. The electrodes interact with the elements to transduce between acoustic and electrical energy. The variation of potential or distance between electrodes across an element causes electrical signal generation or acoustic energy, respectively.

In one embodiment shown in FIG. 4, flex circuit 60 resides between the backing block and the PZT of the array 12. The flex circuit 60 bends around the side of the backing block and is folded (in an accordion fashion) behind the backing block. Within the flex connection bundle (accordion), the flex circuit 60 is connected to a bundle of conductors 16 that carry the signals between the beamformer 52 and the array 12. In one variation, the flex connection bundle resides between the backing block and the can 14.

The elements 24 contain piezoelectric material. Solid or composite piezoelectric materials may be used. Each element is a rectangular solid, cube, or six sided, but other surfaces may be provided. For example, the emitting face of one or more elements 24 is concave or convex for elevation focusing or frequency based directivity. Alternatively, a microelectromechanical device, such as a flexible membrane, is used. Any now known or later developed ultrasound transducer may be used.

Any number of elements 24 may be provided, such as 64 elements. 128 or other number of elements 24 may allow for larger apertures and/or a greater number of apertures. The elements 24 are adjacent to each other, such as having substantially a wavelength or less spacing between the centers of adjacent elements 24. For example, the elements 24 have half wavelength spacing with kerfs acoustically separating each element 24. Sparse arrays 12 with greater spacing between elements 24 may be used.

The elements 24 are positioned along an azimuth axis. For a one-dimensional array 12, the elements 24 are in a single row along the azimuth axis. The array 12 may be linear or curved linear. A curved linear array 12 has ends or a middle that extend towards or away from the azimuth axis, but the elements 24 are still positioned along the azimuth dimension. Due to the curve, some elements 24 of the array 12 are at different depths or ranges. For use in a catheter, the azimuth axis is along the longitudinal axis of the catheter 50, but may be offset from the axis or centered along the axis. The array 12 of the elements 24 is of any length, such as 7 mm, 14 mm, or 28 mm.

Multi-dimensional arrays 12 may be used. For example, two or more rows of elements 24 are adjacent to each other along the elevation dimension. 1.25, 1.5, 1.75 or 2D arrays may be provided. The spacing between elements 24 along the elevation dimension is the same or different than along the azimuth dimension, such as a 2×64 array with half wavelength spacing between all adjacent elements in azimuth. The elements are long in elevation, such as having a 3-20 wavelength elevation width, but may have half wavelength or other spacing.

In one embodiment for volume imaging with the array from a thin and long catheter, the array 12 twists about the longitudinal axis of the array or a longitudinal axis spaced from the center of the array. Different elements 24 or groups of elements 24 face in different directions. The change in direction along the length of the array 12 is gradual, but may have any step size. For example, the twist follows a helical pattern. By walking an aperture along the array, different scan planes spaced or fanned apart in elevation are defined and used for scanning. This allows scanning of a volume with the linear array.

The helical or other twist of the array 12 about any longitudinal axis is created by forming the stack and twisting the stack and/or by assembling the elements 24 in the desired relationship. In one embodiment represented in FIG. 4, the transducer stack including the elements 24 is formed on or connected to a memory metal, such as Nitinol. Once cured and/or bonded with the memory metal in a flat configuration, the memory metal is forced by temperature or other energy to return to a twisted configuration. This twists the arrangement of the elements 24.

The side of the elements 24 covered by the matching layer, closer to the region to be scanned and/or opposite the backing block, is the emitting face of the array 12. Acoustic energy is transmitted from and received at the emitting face of the array 12. The angle of acoustic energy relative to the emitting face affects the sensitivity of the elements 24 to the energy. The elements 24 are more sensitive to the energy at normal incidence to the elements 24.

Electrical conductors 16 connect the elements 24 of the array 12 to the receive beamformer 52. The conductors 16 are cables, coaxial cables, traces on flexible circuit material, wires, flex circuits, wire jumpers, combinations thereof, or other now known or later developed conductor. One conductor 16 is provided for each element 24. Alternatively, fewer conductors 16 than elements 24 may be used, such as for switched apertures, partial beamforming, or multiplexing. The conductors 16 are separately addressable. Each element 24 may be selectively used for a given aperture and associated electronic steering. Alternatively, some elements 24 are useable with only a subset of possible apertures.

The array 12 is positioned within the catheter 50. The array 12 may fit within 10 French, 3.33 mm, 12.5 French, or other diameter catheter 50. The conductors 16 are routed through the catheter 50 to the beamformer 52. The catheter transducer is used for imaging. The images assist in diagnosis, catheter or tool guidance, and/or therapy placement.

The markers 58 in the catheter 50 are radio-opaque. Tungsten, silver, gold, stainless steel, tantalum, or other material may be used. The markers 58 are cylinders, but may be other shapes (e.g., spherical, conical, plate, wire, or cube). The markers 58 are any size, such as 0.5 mm diameter cylinder with a 0.5 mm height. For example, 1 mm tantalum spheres are used as markers.

Two markers 58 are shown in FIG. 1. In other embodiments, only one or more than two markers 58 are used. For example, six markers 58 could be used.

The markers 58 are spaced along the catheter 50. As shown, the markers 58 may be positioned adjacent to, but not behind, the array 12. One marker 58 is distal to the array 12, and another marker 58 is proximal to the array 12. Only proximal or only distal markers 58 are provided in other embodiments. Where more than one marker 58 is provided distal or proximal to the array 12, the markers 58 may have an even or variable distribution, such as markers every 2-6 mm. In one embodiment, five markers 58 are placed distal to the array 12 and two markers 58 are placed proximal to the array 12. In alternative embodiments, one or more markers 58 are positioned under or behind the array 12. The markers 58 may be beside or to the sides of the array 12 rather than or in addition to the proximal and/or distal ends. In yet other embodiments, markers 58 are not provided on or in the catheter 50 or are positioned behind the array.

To assist in aligning the array 12 relative to the catheter 50 and/or markers 58, the array 12 is keyed to a can 14 (see FIGS. 2 and 3). For example, the helically twisted array 12 of acoustic elements mounts to the support (e.g., can 14) with an orientation defined by at least two mating surfaces of the helical twisted array 12 and the can 14. In the example represented in FIGS. 3 and 4, the mating surfaces including extensions 62 (e.g., keys) and matching depressions 64, 66 (e.g., ways). While the extensions 62 are shown on the array 12 and the matching depressions 64, 66 are shown on the can 14, the reverse may be provided or combinations of both (e.g., extension 62 and depression 64, 66 on the array 12).

For keyed fitting, the two surfaces have varying shapes that match each other so that the can 14 and the array 12 may be positioned in a limited number of orientations relative to each other, such as just one or two orientations. For example, the shaped surface on the array is an extension having a greater width than height where length is the measure of extension away from the array 12. An oblong, elliptical, rectangular or other cuboid or shape may be used (e.g., N-sided prismoid). By have multiple shaped surfaces (e.g., multiple extensions or depressions), the multiple pairs of mating surfaces may be used to limit the number of orientations. For example, a square or equal sided cube may be used as extensions where the multiple cubes are at different angles of rotation relative to the array 12 and/or distributed in a pattern limiting the fit of the array 12 to the can 14 to just one or two orientations despite the equal sided cube by itself limiting to just four orientations.

The extension 62 or depression 64, 66 may be provided on any part of the array, such as from the sides, ends, and/or bottom. While extending at a normal to a surface of the array 12, non-normal angles of extension may be used.

FIG. 4 shows an example where two rectangular extensions 62 are provided on opposite ends of the array. In this example, the memory metal extends beyond the elements 24 to form the extensions 62 from the array 12. Where the array 12 is a twisted array using the memory metal, each of the extensions 62 may be at a different angle about the longitudinal axis of the array 12, providing a more limited keying of the array 12 orientation to the can 14. Other extensions than the memory metal, such as from the backing block, bonded on parts, or other carrier, may be used.

The catheter housing 18 is sealed over the markers 58, the array 12, and the can 14. The catheter housing 18 is a sleeve of plastic or other material for insertion into a patient. For example, the catheter housing 18 is formed from Pebax. Other materials, such as other Nylons or biologically neutral (or biocompatible) materials, may be used.

The catheter housing 18 is placed over the array 12 and can 14, after the array 12 and can 14 are connected together. The catheter housing 18 slides over the array 12, can 14, markers 58, and some of the extent of the cables 16. In one embodiment, the catheter housing 18 is plastic welded as a thermoplastic around the array 12 and can 14. Epoxy or other bonding agent may be provided between the catheter housing 18 and the array 12. Multiple layers of housing material may be used, such as one layer for electrical insulation and another for the outer surface of the catheter 50. In other embodiments, the catheter housing 18 is in multiple pieces. Each piece connects to an end of the can 14. Plastic welding is used to connect the pieces. Window material is formed by melting material over the array 12. In yet other embodiments, an injection molding process is used where the catheter housing material flows over and around the can 14 and the array 12. The window may be formed by casting or dipping in other embodiments.

After sealing, the catheter 50 may be used for imaging. Referring again to FIG. 1, the array 12 connects to the beamformer 52 for imaging. The beamformer 52 includes a plurality of channels for generating transmit waveforms and/or receiving signals. Relative delays and/or apodization focus the transmit waveforms or received signals for forming beams. The beamformer 52 connects with the conductors 16. The beamformer 52 selects an aperture including one, some, or all of the elements 24 of the array 12. Different apertures may be used at different times. The aperture is formed by using the elements 24 for transmit and/or receive operations while not using other elements. The beamformer 52 is operable to scan from a plurality of apertures formed by adjacent groups of the elements 24. The apertures may walk through regular increments or skip to different portions of the array 12.

For scanning, the beamformer 52 electronically focuses along the azimuth direction. A plurality of scan lines using an aperture is scanned. During receive operations, the focus may vary as a function of depth (i.e., dynamic focusing). An elevation focus is provided by a lens and/or element sensitivity, or the array 12 is not focused in elevation. In alternative embodiments, the beamformer 52 connects with elevation spaced elements for at least partial electric focusing and/or steering in the elevation dimension.

The image processor 54 is a detector, filter, processor, application specific integrated circuit, field programmable gate array, digital signal processor, control processor, scan converter, three-dimensional image processor, graphics processing unit, analog circuit, digital circuit, or combinations thereof. The image processor 54 receives beamformed data and generates images on the display 56. The images are associated with a two-dimensional scan. Alternatively or additionally, the images are three-dimensional representations. Data representing a volume is acquired by scanning.

Using the markers 58, the array 12 may be located in other imaging. For example, x-rays for fluoroscopy are transmitted through the patient with the catheter 50 in the patient. The markers 58 are radio-opaque, so appear as bright or contrast objects in the fluoroscopic image or detected data. Since the position of the array 12 relative to the markers 58 is known, the location and/or orientation of the array 12 is determined from the markers 58.

FIG. 2 shows different parts of the catheter 50 used in a system for manufacturing the medical ultrasound imaging catheter. The parts are the array 12, the can 14, and the catheter housing 18. Additional, different or fewer parts may be provided. For example, steering wires are provided. The array 12 includes cables or wires 16, and the can 14 includes markers 58. In other embodiments, the markers 58 are separate from the can 14 or no markers are provided. The catheter housing (or tip) 18 is shown as a tube for sliding over and shrink wrapping (e.g., tipping) around the array 12 and can 14, but may have other shapes, sizes, and/or forms for creating the catheter 50. The tip of the catheter housing 18 may be plastic welded in place where a wrap is applied over the array kerfs to prevent the tip material from intruding into the kerfs.

The can 14 is an insert, support, or other structure for stiffening the array 12. The can 14 is a material in addition to the transducer stack. The transducer stack of the array 12 includes the matching layer, electrodes, flexible circuits, and backing block. The can 14 may incorporate the backing block and/or signal traces for connecting the electrodes to the cables 16 or may not. The can 14 extends beyond the array 12, such as distally and/or proximally along the axis of the catheter 50 being assembled. Alternatively, the can 14 is a same length as or shorter than the array 12. Side walls of the can may cover two or more sides or ends of the array 12. The can 14 is a separate component from the array 12 and incorporates a keyed surface, such as a key or way surface. Since the shaping of the surface is not optimal for a transducer element 24 and backing may not be sufficiently stiff or durable, a separate structure is provided.

The can 14 is plastic, but other materials may be used. In one embodiment, the can 14 is formed from high Tg (glass transition temperature) plastic (e.g., PSU Tg=190 C), such as Nylon, filled Nylon, or Radel. The melt temperature is 10 degrees or more above the melt temperature of the catheter housing 18, such as being substantially higher than the melt temperature of Pebax. The greater melt temperature may avoid compromising the can 14, array orientation, and/or marker placement during subsequent tipping of the catheter. By having a greater melt temperature, the can 14 does not flow or reach a melting point even when the catheter 50 is heated to form the catheter housing 18. The can 14 may not change shape, changes shape very little, or changes shape in a planned way during the plastic welding, molding, tipping, or casting used to fabricate the catheter 50.

The can 14 includes a cavity 22. The cavity 22 is sized to accept without pressure or with a press fit around part of the array 12. The array 12 may be set in or pressed into the cavity 12. Beams, walls, or other structure on at least two sides hold the array 12 by friction, snap fit, or other connector. In one embodiment, the cavity 22 press fits with the array 12 on four sides. The cavity 22 may instead be oversized relative to the array 12. A connector or adhesive holds the array 12 to the can 14, such as on a side wall or bottom surface of the cavity 22. In yet other embodiments, the can 14 is free of a cavity for the array 12, and the array 12 connects to a top surface of the can 14. The cavity 22 may be a hole in the can, surrounding the array 12 on only 2-5 sides.

The can 14 is more rigid than the array 12. For example, the plastic or other material bends less than the array 12 in response to the same stress along the longitudinal axis. Beams, ridges, insert rod(s) (see FIG. 10), or other structure in addition to or as an alternative to more rigid material may be used to make the can 14 more rigid than the array 12. By connecting the can 14 to the array 12, the geometry established by the can 14 may assist in imaging. Maintenance of the array 12 as flat, curved, twisted, or some other shape within the catheter 50 may reduce imaging artifacts and/or allow sector scanning. The bow or buckling of the array 12 may be minimized by introducing the can 14 as a reinforcing member. The can 14 may reduce any curvature along the longitudinal axis of the array or may enforce a desired curvature or helical surface.

Figure 5:
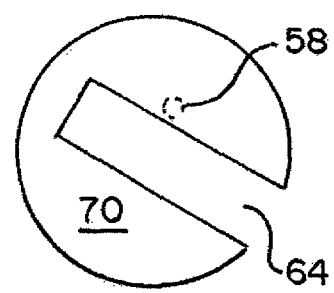
FIG. 5 is an end view of a proximal section of the can of FIG. 3.
Figure 6A:
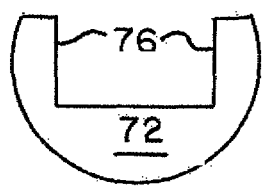
FIGS. 6A-C are cross-sectional views of a center section of the can of FIG. 3.
Figure 6B:
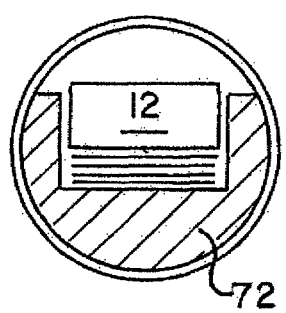
Figure 6C:
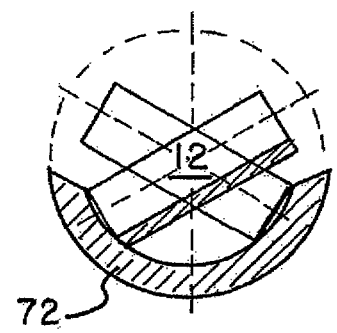
Figure 7A:
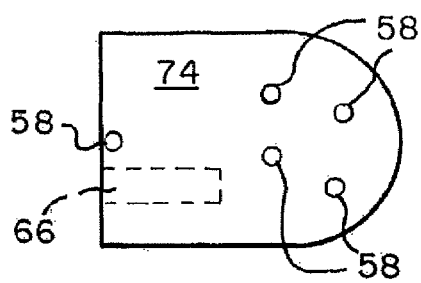
FIGS. 7A and B are a side view and a cross-sectional end view, respectively, of a distal section of the can of FIG. 3.
Figure 7B:
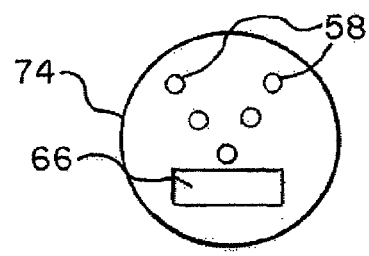
Figure 8:
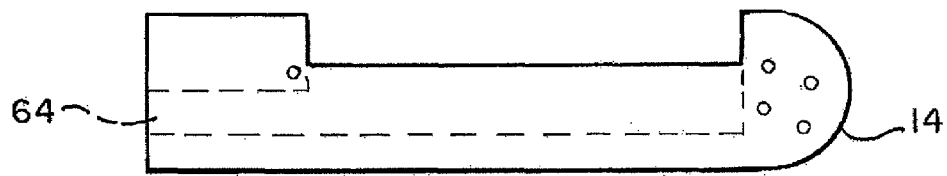
FIG. 8 is a side view of the can of FIG. 3.

In one embodiment, the can 14 is a single part, such as an injection molded piece. FIG. 3 shows the can 14 as a single part. In other embodiments, the can 14 is formed from separate parts connected or assembled together. FIGS. 5-8 show the can 14 as three parts. Each part is created using molding, but different techniques may be used for different parts. Each part is of the same material, such as Nylon, but different materials for different parts may be used. FIG. 5 shows a proximal section 70 (e.g., tail piece), FIGS. 6A-C show a center section 72, and FIGS. 7A-B show a distal section 74 (e.g., nosecone). Only two or four or more parts may be used. FIG. 8 shows the parts assembled into a single piece with a same configuration as the can 14 of FIG. 3. The parts are assembled by plastic welding, melting, or adhesive bonding.

Referring to FIGS. 3, 5, and 7A-B, the can 14 includes one or more shaped surfaces for keyed fitting with the array 12. The shaped surface is shaped to fit with or mate with the shaped surface of the array 12. This mating enforces an orientation of the array 12 relative to the can 14. In the embodiment shown in the figures, an indentation 66 is formed as a depression surface in the can 14. An extension 62 of the array 12 mates with the indentation 66. For example, the extension 62 fits snuggly or loosely in the indentation 66.

Another form of depression shown in the figures is a through slot 64. The indentation 66 of FIGS. 7A and 7B encloses the extension, such a surrounding the extension 62 on all sides but one, the side from which the extension 62 is inserted. Conversely, the through slot 64 only contacts two, three, or four sides of an extension 62. FIGS. 3 and 5 shows the through slot 64 having three open sides. One side is adjacent the array 12. Another open side is opposite the array 12 so that the flexible circuit 60 and/or the conductors 16 may extend through the slot 64 and into other proximal parts of the catheter 50. Yet another open side is around an outer circumference. This open side allows one extension 62 of the array 12 to be placed in the indentation 66 while the other extension 62 slides into the slot 64, providing easy assembly of the array 12 with the can 14 without bending the array 12.

Figure 14:
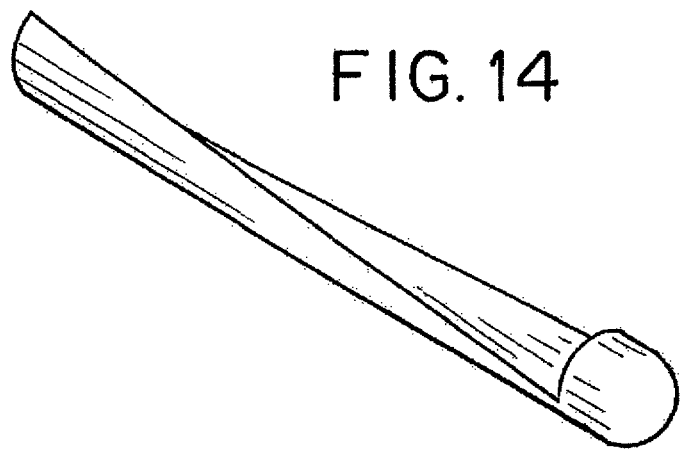
FIG. 14 is a perspective view of one embodiment of an insert with a wall following a helical pattern.

Other shaped surfaces may be used, such as shaping a bottom and side walls 76 of the cavity 22 in a helical surface to mate with the helical surface of the array 12. FIG. 14 shows an example. The side walls do not extend about a point that is greater than 45 degrees above horizontal from the face of the array 12 at any given azimuth position along the array 12. This limits or avoids acoustic interference by the side walls 76. The side walls 76 incorporate a twist or curvature to match the array 12.

Any combination of shaped surfaces may be used. For example, only enclosed indentations 66 are used, only through slots 64 are used, or only curved bottom surface of the cavity 22 is used. As another example, any combination of one or more of indentation 66, through slots 64, and/or curved bottom surfaces are used. In one embodiment, the keying is provided using parts of the array 12 provided for other purposes, such as the twisted surface and/or the twisted memory metal extensions.

The shaped surfaces of the array 12 and the can 14 establish a known relationship of the array 12 to the can 14. The orientation or facing direction of the array 12 is keyed to the can 14. The emitting face of the array 12 faces away from the can 14 in a particular direction due to the keyed surfaces, providing precise alignment of the ultrasound image to the x-ray markers 58 in the can. As an example, FIG. 6C shows the array 12 at two extremes of helical rotation in the center section 72. The array 12 is at these extremes simultaneously, such as at both ends of the array 12. FIG. 6B shows the array 12 at a center of the center section 72. Due to the helical rotation of the emitting face of the array 12, the orientation varies along a length of the can 14 and array 12.

Referring to FIGS. 2, 3, 5, and 7A-B, one or more x-ray opaque markers 58 are positioned in the can 14. By precisely placing holes for the markers 58 or the markers themselves, the keyed orientation of the array 12 relative to the markers 58 in the can 14 is known. In the example of FIG. 3, six holes for corresponding markers 58 are shown, but other numbers in different arrangements may be used.

The markers 58 are placed in apertures or holes cast, drilled, or formed in the can 14. For example, the markers 58 are pressed into the apertures and/or bonded in place. The distal portion 74 of the can 14 extending beyond the array 12 is used to support the markers 58. Similarly, the proximal portion 70 supports one or more markers 58. The bottom or portion under the array 12 may alternatively or additionally support one or more markers 58. Alternatively, the markers 58 are formed in the can 14, such as being cast in the can 14.

In yet other embodiments, the markers 58 are bonded to the can 14 without placement in an aperture.

Since the can 14 is positioned and connected with the array 12 in a keyed manner, the position of the markers 58 relative to the array 12 is established with precision. The can 14 captures the array 12 during assembly of the catheter 50, as well as to create an extended rigid body that contains the markers 58. The markers 58 are precisely positioned prior to plastic welding the acoustic array 12 to the catheter housing 18. The radio-opaque markers 58 may be accurately attached to the can 14.

Figure 9:
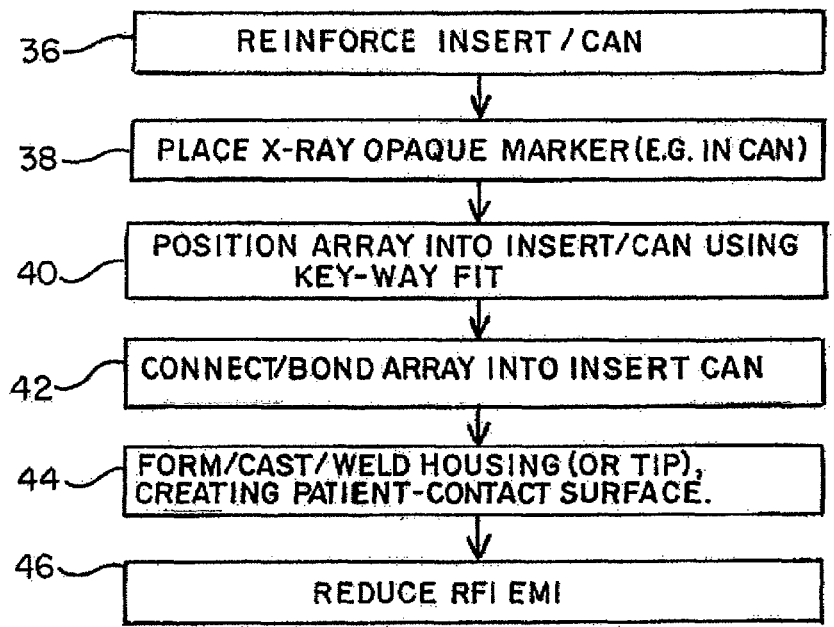
FIG. 9 is a flow chart diagram of one embodiment of a method for manufacturing an acoustic imaging catheter with a keyed insert.

FIG. 9 is a flow chart diagram of one embodiment of a method for manufacturing a medical ultrasound imaging catheter. The method is used to create the catheter of FIG. 1 or 2 or another catheter. Additional, different, or fewer acts may be provided. For example, the reinforcing insert of act 36 is not provided, such as where the insert (e.g., can 14) itself is sufficiently stiff or incorporates ridges or other stiffening structures. As another example, act 38 is not performed where the insert already includes or was formed with markers or where markers are not used. In another example, act 46 is not performed. In yet another example, acts 40 and 42 are combined as one act, such as where placement of the array as a snap or press fit with the insert provides the connection.

The acts are performed in the order shown or a different order. For example, act 38 is performed prior to act 36.

Figure 10:
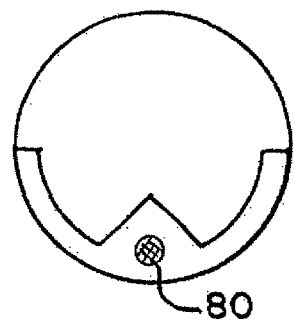
FIG. 10 is a cross-sectional end view of one embodiment of a can with a stiffening rod.

In act 36, the insert is reinforced with one or more stiffening rods or other structures. FIG. 10 shows one example. A reinforcing rod 80 extends along the longitudinal direction of the insert to provide increased rigidity and strength. The triangular cross section containing the rod 80 allows for the helical rotation of the array within the insert while providing a region to house the rod 80. The rod 80 is any material, such as stainless steel, graphite, ceramic, or aluminum oxide. The rod 80 may be x-ray opaque material (e.g., tantalum or silver) to act as a marker. In other embodiments, an I-beam or other shape is used instead of a rod. In yet other embodiments, a stiffening rod 80 is not provided in or on the insert.

In act 38, one or more x-ray opaque markers are placed in or on the insert. For example, a marker is inserted within each marker aperture. The marker is inserted using a pick and place process, such as by a robot or gravity feed device. Alternatively, the markers are manually inserted into the marker apertures.

While x-ray markers are described herein, other types of markers may be used. For example, the catheter is to be detected in magnetic resonance imaging, optical imaging, or other imaging using non-x-ray radiation. Markers of material with high contrast or opaque to the type of imaging are added to the catheter using the added insert or can.

At least some of the markers are adjacent to the array. The markers may contact the array, be spaced within 3 mm, or be at another distance from the array. Any distribution of markers may be used, such as to spatially distinguish position of the catheter when viewed from any or a variety of directions.

In act 40, an insert is positioned adjacent to a transducer array. The array is placed against or in the insert. For example, the transducer array is placed or pressed into a cavity of the insert. Fiducials, guides, rails, posts, holes, or other structures may be provided for positioning the insert relative to the array.

The insert and the array mate or slide together in one relative position. Keyed mating orients the transducer array relative to the insert. For example, one extension on the array is slid or pressed into an indentation or aperture of the insert. Another extension on the array, such as opposite the first extension, is slid into a slot during the insertion. By mating the matched or keyed surfaces, the array is oriented within the insert. Any number of keys and ways may be used. In other embodiments, the keys extend from the insert and the ways are in the array. Combinations of keys and ways on each of the insert and the array may be used. The keys and ways are at any position on the array and insert, such as at the ends.

For a volume ICE imaging catheter, the keys and ways are provided as part of the twist in the array. In one embodiment, the memory metal or other support used to hold the array during creation is used to form the extensions or other keyed surface. One extension on one end of the array fits into an aperture or hole on the insert. Another extension on an opposite end of the array slides along an open or through slot to align the longitudinal axis of the array with the insert. The keys and ways at the different ends have different angles of rotation about the longitudinal axis of the transducer array, but may be at a same angle of rotation. Where the memory metal for a twisted array is used, the helical twist of the array provides the different angles at different ends.

In an alternative or additional embodiment, the keyed surface is formed by the cavity of the insert in which the array is placed. The shape of the array may be other than flat, so the shape of the array itself may be used. For example, the array twists, such as in the helical pattern. The insert includes a surface to match the surface formed by the twist. The side walls and/or the bottom surface have a mating twist. For example, the cross-section of a center section of the insert follows the array twist in order to provide additional rigidity and alignment. By positioning the array between the side walls on the bottom surface, the mating surface of the insert orients the array. FIG. 14 shows an insert with such keyed mating side walls.

In the embodiment represented by FIGS. 6B, 6C, 10, and 11, the bottom surface and/or the side walls do not mate or key to the array. Instead, fill, such as epoxy, plastic, or other bonding material fill the space left by the curved surface of the array fitting against the flat bottom and/or side walls.

Figure 13:
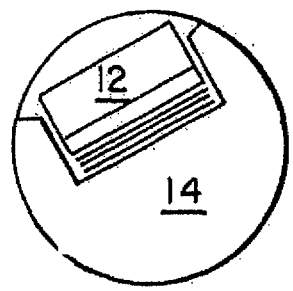
FIG. 13 is a cross-sectional view of a center section of a can with an off-center placement of the array.

The array fits within a majority of the insert in cross-section. The center longitudinal axis of the insert passes through the array, such as being at or near the longitudinal axis of the array. In another embodiment, the cavity of the insert and transducer array within the cavity are off-center from the center longitudinal axis of the insert. FIG. 13 shows an example. This off-axis placement where the center axis of the insert does not pass through any of the array may result in a thinner covering of window material over the array. A larger insert and/or smaller array are placed close to the surface of the catheter. Reducing the window thickness may improve the acoustic performance of the catheter, especially at higher frequencies.

The window material is the catheter housing, such as Pebax 35d or other material. In another embodiment, a window is formed without being part of a sheath or flow of catheter housing. The window material is formed over the array. The window material may be graduated, such as including an intermediate layer of Pebax 40d between the array and the outer layer of Pebax 35d. This window material is separate from the remaining housing of the catheter. The window material fuses to the insert. For example, the insert is made from biologically inert material, such as Nylon. The ends of the insert are fused to other parts of the catheter in a multi-piece construction. The catheter housing fuses to the ends of the insert.

The placement of the insert against the array positions one or more markers relative to the array. For example, one or more markers are in the insert against or adjacent to the cavity. By placing the array in the cavity, the marker is positioned adjacent to the array. The marker is adjacent to the transducer array in a distal or proximal direction relative to the medical ultrasound imaging catheter. The marker may instead be beside or under the array.

In act 42 of FIG. 9, the transducer array is connected with the insert. The connection is through latches, snap fit, other connectors (e.g., screw), bonding, heat sealing, creating the catheter housing over the array and insert, and/or with a press fit. For example, the transducer array is placed in cavity of the insert with bonding material (e.g., adhesive) as part of positioning. The array then connects to the insert by bonding, such as with epoxy cured at room temperature or higher temperatures (e.g., 50 degrees Celsius). After stacking the insert with the array, the stack is pressed and cured to fix the array to the insert. The adhesive is applied before positioning the array against the insert. Alternatively, the adhesive is applied after positioning, such as for formation of the catheter housing. Any bonding material may be used, such as high Tg (e.g., UV curable) adhesive.

Figure 11:
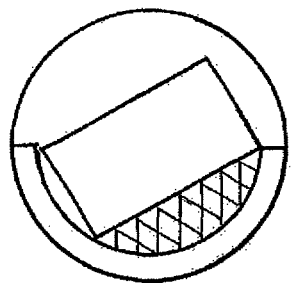
FIG. 11 is a cross-section view of a center section showing bonding of an array in a can.

This bond may reinforce the array by filling the cavity between the array and the insert (see FIGS. 6B and 11). Filling with bonding agent may also reduce the flow required for forming the catheter housing. The connecting fixes the transducer array to the insert. The array does not move or only has limited movement relative to the insert after the fixing. The fixing occurs before or after addition of the catheter housing.

The insert connects with the array directly or through one or more other components. For example, the insert is stacked with an array of matching layer, transducer material, and backing block. Conductors, such as a flexible circuit extend from between the transducer material and the backing block. The bundle or accordion bundle of flexible circuit material is positioned behind the backing block. The insert is stacked directly against the backing block or the bundle/accordion of flexible circuit material is between the insert and the array.

In act 44 of FIG. 9, the catheter housing is formed with the transducer array as oriented with the insert. The housing is formed over the transducer array, insert, and any markers in the insert. The transducer array and insert are placed into the housing, such as sliding a sleeve of housing material over the array. By heating the housing substantially to a melting point of the housing, the catheter housing flows into gaps and over the components of the catheter. Since the insert has a higher melting point than the Tg of the housing, the insert maintains position relative to the array. The insert and array remain flat or in a same shape despite the heating of the catheter housing.

Some portions of the catheter housing 18 before assembly and/or after assembly may be thicker. Thicker material may be used to provide more rigidity. In extruding the catheter housing, forming thicker regions may be difficult. Thin wall sections are desired around the sides of the array. It is difficult to move plastic via injection molding to form thick wall sections beyond the thin wall sections. The insert does not require thick wall sections, so the tip or housing may be easier to manufacture. Using the insert for rigidity may avoid providing a thicker housing for a large region that may otherwise use a thicker housing. Alternatively, thicker housing material is provided for around the insert.

The catheter housing is sealed around any markers and/or the array. Additional housing material, such as plastic (e.g., Pebax), is added to cover the marker and hole and/or the array. The material is the same or different than the material used to form the catheter housing. Alternatively, no additional material is added.

Figure 12:
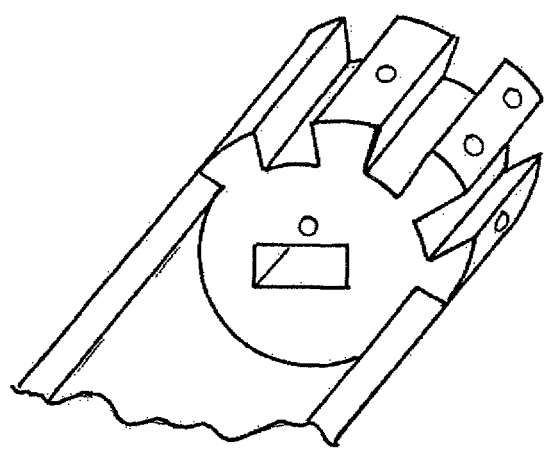
FIG. 12 is a perspective view of one embodiment of a distal section of a can with slots for flow of housing (e.g., catheter tip) material.

In forming the catheter housing, the housing material flows around the insert and array. Due to the gaps or other spaces around the array, more material may flow to that portion of the catheter. To assist in flowing material, one or both ends of the insert may have one or more grooves or slots. FIG. 12 shows one example where slots or grooves are provided near where the face of the array would be located in the insert. The window and housing material flows, in part, through the through slots to the transducer array. The ribs between the slots allow for marker placement holes. The slotted distal section does not interfere with the array keying.

In alternative embodiments, a viscous material, such as ultra-violet curable silicone, is added and cured to seal. Epoxy or other sealing adhesives may be used without heating to avoid further change in the array position within the catheter or further melting of the catheter housing.

In another embodiment, the catheter housing is fused to the ends of the insert. Rather than covering the insert, plastic welding or adhesive is used to connect proximal and distal parts of the catheter to the respective ends of the insert.

By creating the imaging catheter with the insert, the transducer array is maintained substantially rigid. While the insert and connected array may bow or bend under some stresses during use, the array bends less or requires greater force to bend due to the connected insert. Since the insert is more rigid than the transducer array, the array may be held in a more consistent configuration during introduction of the catheter into the patient. The imaging catheter is more resistant to buckling due to the insert being more rigid than the array. This added rigidity may also apply during the tipping process where high hydrostatic pressures and sometime off-axis compressive forces bend, bow, or otherwise distort the array. Fewer image artifacts may result.

In act 46 of FIG. 9, the insert is used to reduce radio frequency interference. The insert is formed from metal or includes metal. For example, the insert is plated. As another example, metal flakes or particles are distributed within or on a surface of the insert, such as a filled Nylon. The metal reduces EMI and/or RFI. In alternative embodiments, metal is not provided in the insert.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for manufacturing a medical ultrasound imaging catheter, the method comprising:
    positioning an insert adjacent to a transducer array with a first keyed mating structure of the transducer array keyed to mate with a second keyed mating structure of the insert, the first keyed mating structure and second keyed mating structure having matching surfaces, the mating of the first keyed mating structure with the second keyed mating structure orienting an emitting face of the transducer array in one of only two or fewer directions relative to the insert;
    connecting the transducer array with the insert; and
    forming a housing of the medical ultrasound imaging catheter with the transducer array as oriented with the insert.

2. The method of claim 1 wherein positioning the insert adjacent to the transducer array comprises fitting a key extending from the transducer array into a slot in the insert.

3. The method of claim 1 wherein positioning the insert adjacent to the transducer array comprises mating keys with slots at both ends of the transducer array, the keys and slots having different angles of rotation about a longitudinal axis of the transducer array.

4. The method of claim 1 wherein positioning the insert adjacent to the transducer array comprises placing a first extension into a hole at a first end of the transducer array and sliding a second extension into a through slot at a second end of the transducer array, the hole having a first orientation and the through slot having a second orientation at a different angle about a longitudinal axis of the transducer array.

5. The method of claim 1 wherein the transducer array comprises a twisted array with a helical twist about the longitudinal axis of the transducer array, and wherein positioning the insert adjacent to the transducer array with the mating of the first keyed mating structure comprises positioning the transducer array against a surface of the insert having a mating twist to the helical twist.

6. The method of claim 5 wherein the insert includes side walls and a bottom surface, the bottom surface having the mating twist, and wherein positioning comprises positioning the transducer array between the side walls, the side walls incorporating twist matching the helical twist.

7. The method of claim 1 wherein the transducer array comprises a twisted array with a memory metal, the memory metal extending from ends of the twisted array at different orientations, and wherein positioning comprises using the memory metal extending from the ends in the mating of the first keyed mating structure with the second mating structure.

8. The method of claim 1 wherein connecting the transducer array with the insert comprises bonding the transducer insert to the transducer array after the positioning.

9. The method of claim 1 wherein forming the housing comprises fusing the housing to ends of the insert.

10. The method of claim 1 wherein the insert comprises an end with a plurality of through slots, and wherein forming comprising flowing window material through the through slots to the transducer array.

11. The method of claim 1 further comprising reducing radio frequency interference with electrically conductive material in the insert.

12. The method of claim 1 wherein the insert is more rigid than the transducer array, and wherein forming comprises forming the housing with the insert such that the medical ultrasound imaging catheter is more resistant to buckling due to the insert being more rigid than the transducer array.

13. The method of claim 1 further comprising placing one or more x-ray opaque markers in the insert.

14. The method of claim 1 wherein positioning comprise positioning the transducer array in a cavity of the insert where the cavity and transducer array as positioned are off-center from a center longitudinal axis of the insert.

15. The method of claim 1 further comprising reinforcing the insert with a stiffening rod.

16. A system for manufacturing a medical ultrasound imaging catheter, the system comprising:
    a transducer array having a first shaped surface extending from an end of the transducer array;
    a can having a second shaped surface keyed to the first shaped surface where the first shaped surface and the second shaped surface have matching shapes, the first shaped surface shaped to mate with the second shaped surface such that the transducer array mates with the can in a first orientation; and a catheter housing connected with the can.

17. The system of claim 16 wherein the transducer array twists about a longitudinal axis of the transducer array where the first orientation is of an emitting face of the array away from the can.

18. The system of claim 16 wherein the first shaped surface comprises a first extension having a greater width than height, wherein the second shaped surface comprises an indentation in the can into which the first extension fits, further comprising a second extension on an opposite end of the transducer array and a slot in the can along which the second extension slides for placement of the transducer array against the can.

19. The system of claim 16 further comprising at least one x-ray opaque marker in the can.

20. A medical ultrasound imaging catheter comprising:

a helical twisted array of acoustic elements mounted in a support with an orientation of an emitting face defined by at least two mating surfaces of the helical twisted array and the support, the at least two mating surfaces including an extension and a matching depression that mate together to provide the orientation; and a housing connected with the support.

* * * * *